(12) United States Patent
Song et al.

(10) Patent No.: US 10,179,121 B2
(45) Date of Patent: Jan. 15, 2019

(54) USE OF STATINS IN THE TREATMENT OF ISCHEMIC DISEASES

(71) Applicant: Peking University Third Hospital, Beijing (CN)

(72) Inventors: Chunli Song, Beijing (CN); Yingsheng Xu, Beijing (CN); Jie Tan, Beijing (CN); Qi Guo, Beijing (CN); Can Liu, Beijing (CN)

(73) Assignee: Peking University Third Hospital, Beijing (CN)

( * ) Notice: Subject to any disclaimer, the term of this patent is extended or adjusted under 35 U.S.C. 154(b) by 0 days.

(21) Appl. No.: 15/254,501

(22) Filed: Sep. 1, 2016

(65) Prior Publication Data
US 2018/0055819 A1    Mar. 1, 2018

(51) Int. Cl.
| | |
|---|---|
| *A61K 31/366* | (2006.01) |
| *A61K 9/00* | (2006.01) |
| *A61K 9/08* | (2006.01) |
| *A61K 9/06* | (2006.01) |

(52) U.S. Cl.
CPC .......... *A61K 31/366* (2013.01); *A61K 9/0019* (2013.01); *A61K 9/0024* (2013.01); *A61K 9/06* (2013.01); *A61K 9/08* (2013.01)

(58) Field of Classification Search
None
See application file for complete search history.

(56) References Cited

U.S. PATENT DOCUMENTS

2008/0262074 A1 * 10/2008 Quallich

OTHER PUBLICATIONS

Tan et al., "A single CT-guided percutaneous intraosseous injection of thermosensitive simvastatin/poloxamer 407 hydrogel enhances vertebral bone formation in ovariectomized minipigs", Osteoporosis International, 2016, vol. 27, pp. 757-767, published online Jul. 30, 2015.*
Matsumura et al., "Effects of Atorvastatin on Angiogenesis in Hindlimb Ischemia and Endothelial Progenitor Cell Formation in Rats", Journal of Atherosclerosis and Thrombosis, 2009, vol. 16, pp. 319-326.*
Shantsila et al., "Endothelial Progenitor Cells in Cardiovascular Disorders", Journal of the American College of Cardiology, 2007, vol. 49(7), pp. 741-752.*
Llevadot et al., "HMG-CoA reductase inhibitor mobilizes bone marrow-derived endothelial progenitor cells", Journal of Clinical Investigation, 2001, vol. 108(3), pp. 399-405.*
Zhang et al., "Tumor Progression of Non-Small Cell Lung Cancer Controlled by Albumin and Micellar Nanoparticles of Itraconzole, a Multitarget Angiogenesis Inhibitor," Mol. Pharmaceutics (2017); 14(12):4705-4713.
Yapar et al., "Second trimester pregrnancy termination including fetal death: comparison of five different methods," European Jouranl of Obstretrics & Gynecology and Reproductive Biology (1996); 69:97-102.
Kaul et al., "Paclitaxel-Eluting versus Everolimus-Eluting Coronary Stents in Diabetes," N Engl J. Med (Oct. 29, 2015); 373(18):1709-1719.
Chen et al., "Mifepristone combined with ethacridine lactate for the second-trimester pregnancy termination in women with placenta previa and/or prior cesarean deliveries," Arch Gynecol Obstet (2017); 295:119-124.
Alansari et al., "IV Magnesium Sulfate for Bronchiolities, A Randomized Trial," Ch3st (2017); 152(1):113-119.
Faried et al., "Inhibition of the mammalian target of rapamycin (mTOR) by rapamycin increases chemosensitivity of CaSki cells to paclitaxel," European Journal of Cancer (2006); 42:934-947.
Budhwani et al., "Examining the Use of Magnesium Sulfate to Treat Pregnant Women with Preeclampsia and Eclampsia: Results of a Program Assessment of Emergency Obstetric Care (EmOC) Traning in India," The Journal of Obstretics an dGynecology of India (Sep.-Oct. 2017); 67(5):330-336.
O'Meara et al., "Antibiotics and Antiseptics for venous leg ulcers," Cochrane Database of Systematic Reviews (2014); Issue 1. Art. No. CD003557 (194 pages).
Norman et al., "Antiseptics for burns," Cochrane Database of Systematic Reviews (2017); Issue 7. Art. No. CD011821 (240 pages).
Eloy et al., "Co-loaded paclitael/rapamycin liposomes: Development, characterization and in vitro and in vivo evaluation for breast cancer therapy," Colloids and Surfaces B: Biointerfaces (2016); 14:74-82.
Blanco et al., "Colocalized Delivery of Rapamycin and Paclitaxel to Tumors Enhances Synergisitc Targeting of the PI3K/Akt/mTOR Pathway," Molecular Therapy (Jul. 2014); 22(7):1310-1319.
Chaabane et al., "Biological responses in stented arteries," Cardiovascular Research (2013); 99:353-363.
Chim et al., "Angiogenic factors in bone local environment," Cytokine & Growth Factor Reviews (2013); 24:297-310.
Katsumoto et al., "Biphasic Effect of HMG-CoA Reductase Inhibitor, Pitavastatin, on Vascular Endothelial Cells and Angiogenesis," Circulation Journal (2005); 69:1547-1555.
Papayannopoulou, "Current mechanistic scenarios in hematopoietic stem/progenitor cell mobilization," Blood (2004); 103(5):1580-1585.
Pearson, "Endothelial progenitor cells—an evolving story," Microvascular Research (2010); 79:162-168.
Fadini et al., "Short-term statin discontinuation increases endothelial progenitor cells without inflammatory rebound in type 2 diabetic patients," Vascular Pharmacology (2015); 67-69:21-29.
Madonna et al., "Circulating endothelial progenitor cells: Do they live up to their name?" Vascular Pharmacology (2015); 67-69:2-5.
Li et al., "Endothelial progenitor cells in ischemic stroke: an exploration from hypothesis to therapy," Journal of Hematology & Oncology (2015); 8(33):1-17.

(Continued)

*Primary Examiner* — Savitha M Rao
*Assistant Examiner* — Gregg Polansky
(74) *Attorney, Agent, or Firm* — Fox Rothschild LLP

(57) ABSTRACT

The invention discloses statins compounds used as local intraosseous application for the treatment of ischemic diseases, in particular, discloses local intraosseous application of statin compounds in the treatment of peripheral ischemic diseases or cardio-cerebrovascular ischemic diseases.

12 Claims, 17 Drawing Sheets

(56) References Cited

OTHER PUBLICATIONS

Hristov et al., "Reduced numbers of circulating endothelial progenitor cells in patients with coronary artery disease associated with long-term statin treatment," Atherosclerosis (2007); 192:413-420.
Resch et al., "Endothelial Progenitor Cells: Current Issues on Characterization and Challenging Clinical Applications," Stem Cell Rev and Rep (2012); 8:926-939.
Yamahara et al., "Potential use of endothelial progenitor cells for regeneration of the vasculature," Therapeutic Advances in Cardiovascular Disease (2009); 3(1):17-27.
Fukumoto et al., "Bone as an endocrine organ," Trends in Endocrinology and Metabolism (2009); 20(5):230-236.
Urbich et al., "Endothelial Progenitor Cells: Characterization and Role in Vascular Biology," Circulation Research (2004); 95:343-353.
Miyamoto et al., "Osteoclasts are dispensable for hematopoietic stem cell maintennace and mobilization," The Journal of Experimental Medicine (2011); 208(11):2175-2181.
Fattore et al., "Bone and bone marrow: The same organ," Archives of Biochemistry and Biophysics (2010); 503:28-34.
Pearson, "Endothelial progenitor cells—hype or hope?" Journal of Thrombosis and Haemostasis (2009); 7:255-262.
Rao et al., "Osteoclasts are dispensable for hematopoietic progenitor mobilization by granulocyte colony-stimulating factor in mice," Experimental Hematology (2015); 43:110-114.
Sata, "Biphasic Effects of Statins on Angiogenesis," Circulation (2002); 107(47).
Urbich et al., "Double-Edged Role of Statins in Angiogenesis Signaling," Circulation Research (2002); 90:737-744.
Mosialou et al., "MC4R-dependent suppression of appetite by bone-derived lipocalin 2," Nature (2017); 543:385-408.
Napoli et al., "Therapeutic targeting of the stem cell niche in experimental hindlimb ischemia," Nature Clinical Practice cardiovascular Medicine (2008); 5(9):571-579.
Vincent et al., "Inhibition of endothelial cell migration by cerivastatin, an HMG-CoA reductase inhibitor: contribution to its antiangiogenic effect," FEBS Letters (2001); 495:159-166.
Bogoslovsky et al., "Stromal-Derived Factor-1a Correlates With Circulating Endothelial Progenitor Cells and With Acute Lesion Volume in Stroke Patients," Stroke (2011); 42:618-625.
Llevadot et al., "HMG-CoA reductase inhibitor mobilizes bone marrow-derived endothelial progenitor cells," The Journal of Clinical Investigation (2001); 108(3):399-405.
Weis et al., "Statins Have Biphasic Effects on Angiogenesis," Circulation (2002); 105:739-745.

* cited by examiner

USE OF STATINS IN THE TREATMENT OF ISCHEMIC DISEASES

FIELD OF THE INVENTION

The present invention relates to the field of pharmaceutical biotechnology, more specifically, the new use of HMG-CoA reductase inhibitors (statins) for the treatment of ischemic diseases.

BACKGROUND OF THE INVENTION

Cardio-cerebrovascular diseases cause great harm to human health, and the resulting morbidity and disability is very high. With the aging population and the decline in the age of onset, the problem is more and more serious. At present, the treatment methods of ischemic heart/cerebral blood vessels mainly include drugs, angioplasty and artery bypass grafting. Current randomized control trial (RCT) research shows that positive drug treatment can achieve the same or even better results than the interventional angioplasty treatment (Lampropoulos C E, Papaioannou I, D'Cruz D P. Osteoporosis—a risk factor for cardiovascular disease? Nature reviews Rheumatology. 2012; 8:587-98). This has led us to reflect on the interventional therapy and the exploration of the treatment of revascularization.

Peripheral arterial disease (PAD) is caused by occlusive atherosclerosis in a vascular bed other than the heart. PAD is now known to be an important public health problem with a total prevalence that is nearly equal to that of coronary artery disease (CAD). The prevalence of PAD increases with age, affecting 6% of individuals aged 50-60 years, and 10-20% of individuals aged >70 years. Despite improvements in medical care and revascularization, patients with critical limb ischaemia continue to have a high risk of major amputation (below the knee or higher) and cardiovascular death. The primary goal of therapy in critical limb ischaemia is to achieve blood flow to the distal limb vessels with angioplasty or bypass surgery. However, many patients with critical limb ischaemia are unsuitable for revascularization, the vessels of patients with extensive occlusion cannot be operated at all, and the long-term re-occlusion rate is high.

Bone marrow derived endothelial progenitor cells (Endothelial Progenitor Cells, EPCs) play important roles in angiogenesis and endothelial homeostasis. Therapeutic angiogenesis, also known as "drug bypass", uses exogenous vascular growth factor and bone marrow derived EPCs, to promote angiogenesis in ischemic tissue (Therapeutic angiogenesis for critical limb ischaemia. Nature Reviews Cardiology. 2013; 10:387-3967). However, the limitation of therapeutic angiogenesis is that the number of circulating EPCs is low, and aging, diabetes, hyperlipidaemia and other diseases cause the number of circulating EPCs to be even lower (Yao L, et al. Bone marrow endothelial progenitors augment atherosclerotic plaque regression in a mouse model of plasma lipid lowering. Stem Cells. 2012; 30:2720-2731) (Adler B J, et al. Obesity-driven disruption of haematopoiesis and the bone marrow niche. Nature Reviews Endocrinology. 2014; 10:737-748). It is an important therapeutic strategy to increase the number of peripheral blood EPCs by promoting endogenous EPCs mobilization (Liu Y, et al. Beneficial effects of statins on endothelial progenitor cells. Am J Med Sci. 2012; 344:220-226).

It has been traditionally considered that the skeleton is an inert organ that acts as the storage of calcium and phosphorus, protecting the internal organs. Recent studies have found that bone is an important endocrine organ, which is regarded as paradigm of integrative physiology, not only acts as a target organ, but also acts as an important organ to modulate system functions (Karsenty G, Ferron M. The contribution of bone to whole-organism physiology. Nature. 2012; 481:314-320.) (Karsenty G, Oury F. Biology without walls: the novel endocrinology of bone. Annu Rev Physiol. 2012; 74:87-105). It can also regulate the peripheral vasculature by bone-vascular axis (Thompson B, Towler D A. Arterial calcification and bone physiology: role of the bone—vascular axis. Nature Reviews Endocrinology. 2012; 8:529-543). Bone not only contains osteoblasts, osteoclasts and bone cells, but is also rich in endothelial cells, macrophages, nerves and adipose tissue, and even more enriched in a large number of hematopoietic stem cells and bone marrow stromal stem cells. There are two kinds of hematopoietic stem cell niche, the osteoblast niche and endothelial niche, that cooperatively regulate haematopoiesis stem cell proliferation, mobilization and differentiation (Bianco P. Bone and the hematopoietic niche: a tale of two stem cells. Blood. 2011; 117:5281-5288) (Morrison S J, Scadden D T. The bone marrow niche for haematopoietic stem cells. Nature. 2014; 505:327-334).

In recent years, the pleiotropic effects of statins have attracted more and more attention. However, as inhibitors of the rate limiting enzyme of cholesterol synthesis in the liver, less than 5% of statins reached the circulation after oral administration, and even less reached the bone. We have found that intraosseous injection of statins could promote the secretion of insulin and enhance insulin sensitivity, and increase bone mass, improve bone mineral density and improve bone tissue micro structure, and enhance the mechanical properties of bone (CN201210596032.3, CN201210512630.8).

However, it has not previously been reported that intraosseous application of statins can mobilize endogenous endothelial progenitor cells and promote peripheral angiogenesis.

SUMMARY OF THE INVENTION

New progress in integrative physiology and the new discovery of "bone is an endocrine organ" may provide such a possibility. In particular, the present inventors are the first to appreciate the therapeutic potential of intervening at local bone to achieve the purpose of treatment of systemic diseases. The abundance of trabecular space and the bone marrow cavity provides an excellent space for intervention/local drug delivery.

Here, we found that a single local intraosseous application of a small dose of statins can continuously mobilize endogenous endothelial progenitor cells, significantly promote systemic angiogenesis, and treat ischemic diseases.

Accordingly, one purpose of the present invention is to provide a composition comprising a statin or pharmaceutically acceptable salt thereof in the treatment of ischemic disease. Typically, such compositions are administered locally, preferably intraosseously, into the bone for the treatment of ischemic diseases.

According to the invention, administration of statins or statin-containing compositions locally into bone can promote angiogenesis systemically, and so can be used in the treatment of systemic ischemic diseases, or other conditions which would benefit from an increase in systemic angiogenesis. In particular, as shown herein, the invention can be used to stimulate therapeutic angiogenesis in organs such as the liver, spleen, kidney and pancreas. As a further, non-limiting, example, the invention may be used to facilitate muscle growth, recovery and/or repair, as well as skin and/or wound healing. Without wishing to be bound by any theory, it is believed that the increase in angiogenesis stimulated by the invention enhances the formation of new muscle tissue (in the case of muscle growth, recovery and/or repair), or new skin tissue to repair a wound. Other examples of conditions that may be treated according to the present invention include atherosclerosis. As demonstrated herein, the therapy of the invention can be used to effectively reduce plaque size and formation.

Specifically, the present invention provides a new use of statin compounds for the treatment of ischemic diseases as a single dose for intraosseous administration.

In one specific embodiment of the invention, this invention provides a statin, or a composition comprising a statin or statin compound for use in a method of treatment of ischemic disease, by administration into the bone, wherein the ischemic disease is a peripheral ischemic disease, preferably diabetic acromelic ischemic disease.

In one specific embodiment of the invention, this invention provides a statin or a composition comprising a statin or statin compound for use in a method of treatment of ischemic disease by administration into the bone, wherein the ischemic disease is preferably a cardio-cerebrovascular ischemic disease.

In one specific embodiment of the invention, this invention provides a statin or a composition comprising a statin or statin compound for use in a method of treatment of ischemic disease by administration into the bone, wherein the composition comprises a statin compound or its pharmaceutically acceptable salt in a pharmacologically effective amount and pharmaceutically acceptable adjuvant material.

In one embodiment of the invention, the statin compound comprises, without limitation, simvastatin, atorvastatin, fluvastatin, lovastatin, pravastatin, rosuvastatin, pitavastatin, bervastatin, cerivastatin, crilvastatin, dalvastatin, mevasatin, tenivastatin, or any combination thereof; preferably simvastatin.

The statin compound may be a pharmaceutically acceptable salt, which comprises, without limitation, hydrochloride, hydrobromide, hydriodate, sulfate, nitrate, phosphate, citrate, mesylate, trifluoroacetate, acetate, or a salt of sodium, potassium, calcium, or magnesium thereof.

In one preferable embodiment of the invention, the statin compound is selected from simvastatin, atorvastatin, fluvastatin, lovastatin, pravastatin, rosuvastatin or pitavastatin, and the pharmaceutically acceptable salt thereof, for example hydrochloride, hydrobromide, sulfate, nitrate, phosphate, citrate, mesylate, or a salt of sodium, potassium, calcium, or magnesium thereof; preferably simvastatin, atorvastatin calcium or atorvastatin sodium, fluvastatin sodium, pravastatin sodium, rosuvastatin calcium or pitavastatin calcium.

The present invention also relates to a pharmaceutical composition suitable for intraosseous injection into bone for use in a method of treatment of ischemic disease, wherein said composition contains a statin compound or its pharmaceutically acceptable salt and a pharmaceutically acceptable carrier, diluent or excipient.

In one embodiment of the invention, the statin or composition comprising a statin or statin compound for administration into the bone is preferably for administration via injection into bone or embedding into bone. The statin or composition for administration into the bone may be in the form of injectable dosage forms, wherein the injectable dosage forms include, but not limited to, the injectable solution, injectable suspension liquid, injectable emulsion, injectable gel, injectable solid form, or their slow or controlled release form, or their implant form. Here, the injectable solid form refers to those that is mixed with a solvent such as water for injection, normal saline injection or glucose solution for injection when it is used, to make it feasible for injection.

In one specific embodiment of the invention, the statin or composition comprising a statin or statin compound for administration into bone includes a statins compound or its pharmaceutically acceptable salt and a pharmaceutically acceptable adjuvant or adjuvant material. Here, the pharmaceutically acceptable adjuvant or adjuvant material may be selected from at least one of the optional water-soluble solvent or oily solvent, dispersing agent, isotonic agent, preservative, solubilizer or stabilizers; water-soluble solvent can be selected from distilled water, normal saline, Ringer's solution or phosphate buffer (PBS); oil soluble solvent can be selected from vegetable oil, such as olive oil, castor oil, sesame oil, cottonseed oil or corn oil; dispersing agent can be selected from tween 20 or tween 80, polyethylene glycol, carboxy methyl cellulose, and/or sodium alginate; isotonic agent can be selected from chloride sodium, glycerol, sorbic alcohol, or glucose; Solubilizer can be selected from salicylic acid sodium, poloxamer or acetate sodium; preservative may be selected from methyl paraben, propyl paraben, benzyl alcohol, chlorobutanol, sodium benzoate, or phenol; stabilizer may be selected from albumin, such as human serum albumin, bovine serum albumin, etc. Moreover, said pharmaceutically acceptable adjuvant or adjuvant material may also be selected from biodegradable materials, such as polylactide, poly-L-lactide-glycolide, polyaspartic acid, and so on. For a person skilled in the art, the statin topical composition of the present invention can be prepared through known preparation technology. For example, the statin compound or its pharmaceutically acceptable salt together with dispersing agent, and/or isotonic agent, and/or preservative, and/or solubilizer and/or stabilizers are dissolved, suspended or emulsified in water-soluble solvent or oil-soluble solvent (Remington: The Science and Practice of Pharmacy, 21st edition, 2005, Lippincott Williams, incorporated herein by reference).

The present invention also involves a method of preparing a pharmaceutical composition, comprise a procedure of mixing a statin compound or its pharmaceutically acceptable salt in a therapeutically effective amount with a pharmaceutically acceptable carrier, diluent or excipient; for example, dissolving or suspending the statin compound or its pharmaceutically acceptable salt in a therapeutically effective amount in said pharmaceutically acceptable carrier, diluent or excipient.

In one embodiment of the invention, the dosing interval of the intraosseous administration of the statin medicament to a mammal is once every 7 days up to 600 days, preferably once every 10 to 500 days, more preferably once every 20 to 400 days, most preferably once every 30 to 300 days.

In terms of the intraosseous administration of the statin medicament to a mammal, a single dose of statin compound is from 0.1 mg to 50 mg, preferably from 0.5 mg to 10 mg. A clinician can adjust or modify the frequency and dose of administration according to needs of the clinical effect under the guidance of the present disclosure.

In an embodiment of the invention, the mammal is preferably a human being.

The experimental data herein shows that the local single intraosseous administration of a statin composition described in the disclosure significantly promotes the mobilization of endogenous endothelial progenitor cells, contributes to the angiogenesis in the hind limb ischemia and skin defect model of diabetic rats, and reduces atherosclerosis in ApoE$^{-/-}$ mice. Considering the mobilization of EPCs is seriously damaged in diabetes and hyperlipidemia, it could be believed that local single intraosseous administration of statins or their compositions could be more effective on angiogenesis to treat ischemia, which was verified in the middle cerebral artery occlusion (MCAo) induced cerebral ischemia model. Intraosseous administration of statins or statin compositions acts via therapeutic angiogenesis to treat ischemic diseases and improve microcirculation.

BRIEF DESCRIPTION OF THE DRAWINGS

The present invention will be further explained with reference to the drawings.

FIG. 7-1 shows that the local single intraosseous injection of a small dose of simvastatin improves the angiogenesis after hind limb ischemia in type 1 diabetic rats.

FIG. 7-2 shows that the local intraosseous injection of a small dose of simvastatin accelerates the recovery of blood flow speed in hind limb ischemia of type 1 diabetic rats.

FIG. 8-1 shows an ultrasonic Doppler blood flowmeter demonstrating that oral administration of simvastatin 20 mg/kg/d for 3 weeks did not significantly restore the blood flow velocity in hind limb ischemia of type 1 diabetic rats.

FIG. 8-2 shows that oral administration of high dose of simvastatin could not accelerate the recovery of blood flow speed in hind limb ischemia of type 1 diabetic rats.

FIG. 11A, FIG. 11B: the healing of skin wound, FIG. 11C, FIG. 11D: the capillary density.

FIG. 12A, FIG. 12B: the area of plaque en face, FIGS. 12C-12J: show the affected biochemical parameters, including the area of plaque at aortic root, 12J: the number of EPCs in the circulation.

DETAILED DESCRIPTION OF THE INVENTION

The present invention is described in detail using the examples given below. And it is apparent for a person skilled in the art to make equivalent modification or replacement using the presently disclosed technical features based on the teaching of prior art and the embodiments of this invention, which modifications are considered to be within the scope of the present invention.

PREPARATION EXAMPLES

Preparation of Intraosseous Injective Simvastatin Solution

Simvastatin (1000 mg) was dissolved in 10 ml phosphate-buffered saline (PBS) containing 2% dimethylsulfoxide (DMSO; Sigma, USA) and 0.1% bovine serum albumin (BSA, Sigma, USA), the obtained solution is homogeneous.

Preparation of Intraosseous Injective Thermosensitive Simvastatin Hydrogel

Poloxamer 407 (BASF, Ludwigshafen, Germany; 25% w/w) was added to isotonic phosphate-buffered saline (PBS, pH 7.4, 4° C.) with gentle mixing until complete dissolution.

Gels loaded with simvastatin (National Institutes for Food and Drug Control, Beijing, China) were prepared by adding the drug to the prepared poloxamer 407 solutions. The final simvastatin concentrations were 0, 0.5, or 1 mg/ml.

Example 1

Figure 1:
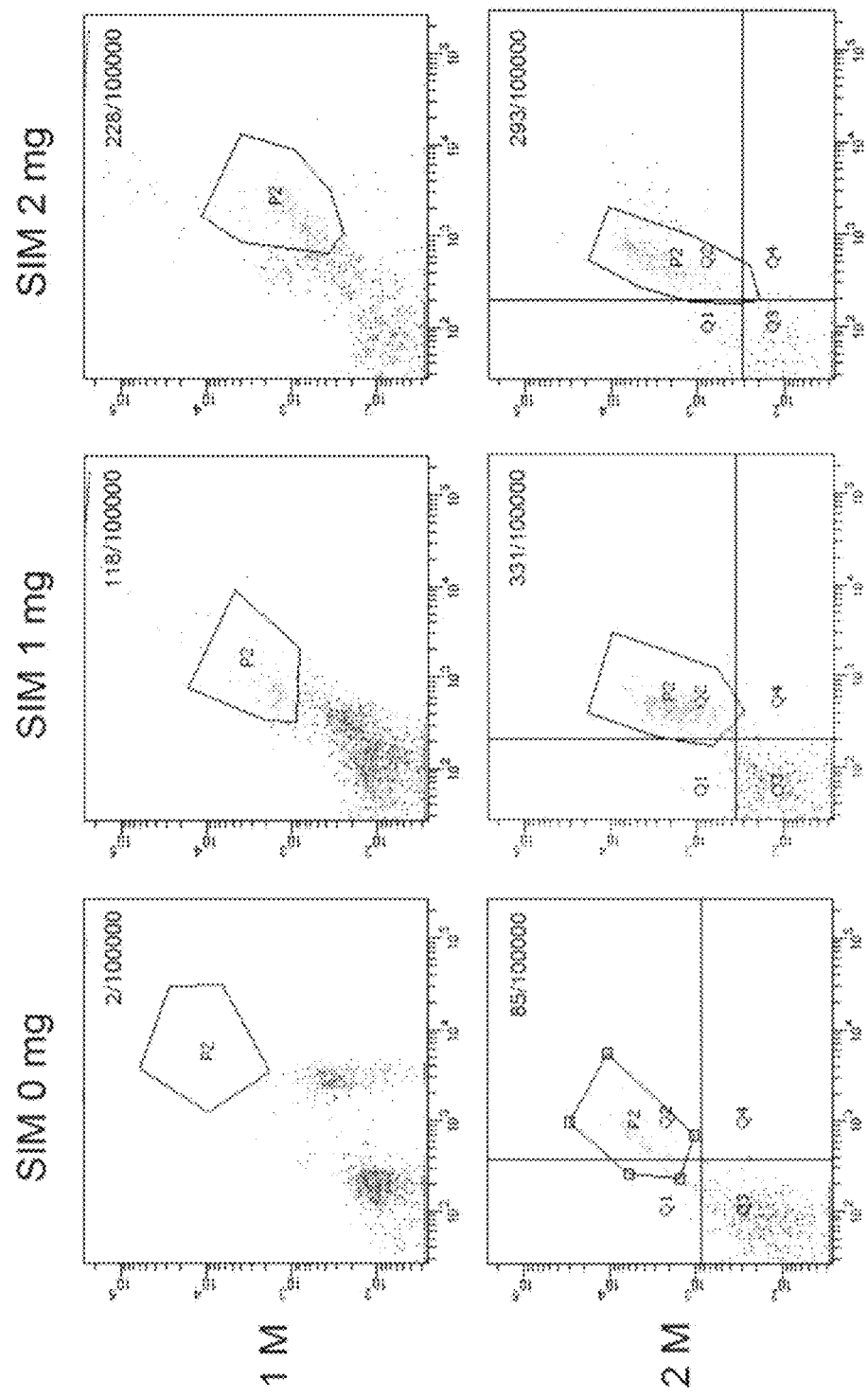
FIG. 1 shows that local single intraosseous injection of a small dose of simvastatin promotes endogenous EPCs mobilization for a long period in type 1 diabetic rats.

Long-Term Mobilization of Endogenous EPCs in Type 1 Diabetic Rats after Single Local Intraosseous Injection of Small Dose Simvastatin In the STZ induced type 1 diabetic rat model, we found that 1 month and 2 months after single local tibial intraosseous injection of simvastatin, the results showed that the circulated number of EPCs in the simvastatin group significantly increased, which was verified by FACS (see FIG. 1).

Example 2

Comparison the Effects of Mobilization of Endogenous EPCs Between Intraosseous Injection of Single Small Dose of Simvastatin and Oral Administration of High Dose Simvastatin in the Hind Limb Ischemia Model of Type 1 Diabetic Rats The right side of the rat femoral artery was removed by 1 cm segment in the STZ induced type 1 diabetic rats. The left tibia received a local single intraosseous injection with 0 mg, 0.5 mg, 1 mg simvastatin respectively, and the number of circulated EPCs was detected by FACS. The results showed that a local single intraosseous injection of simvastatin can significantly increase the number of EPCs in the circulation (P<0.01) (see FIG. 2). However, in the daily administration of 20 mg/kg simvastatin group, the result of FACS showed that the oral administration of high dose simvastatin did not significantly increase the number of EPCs in the circulation (results see FIG. 3). The results implied that different routes of administration of simvastatin might produce different effects.

Example 3

Figure 4:
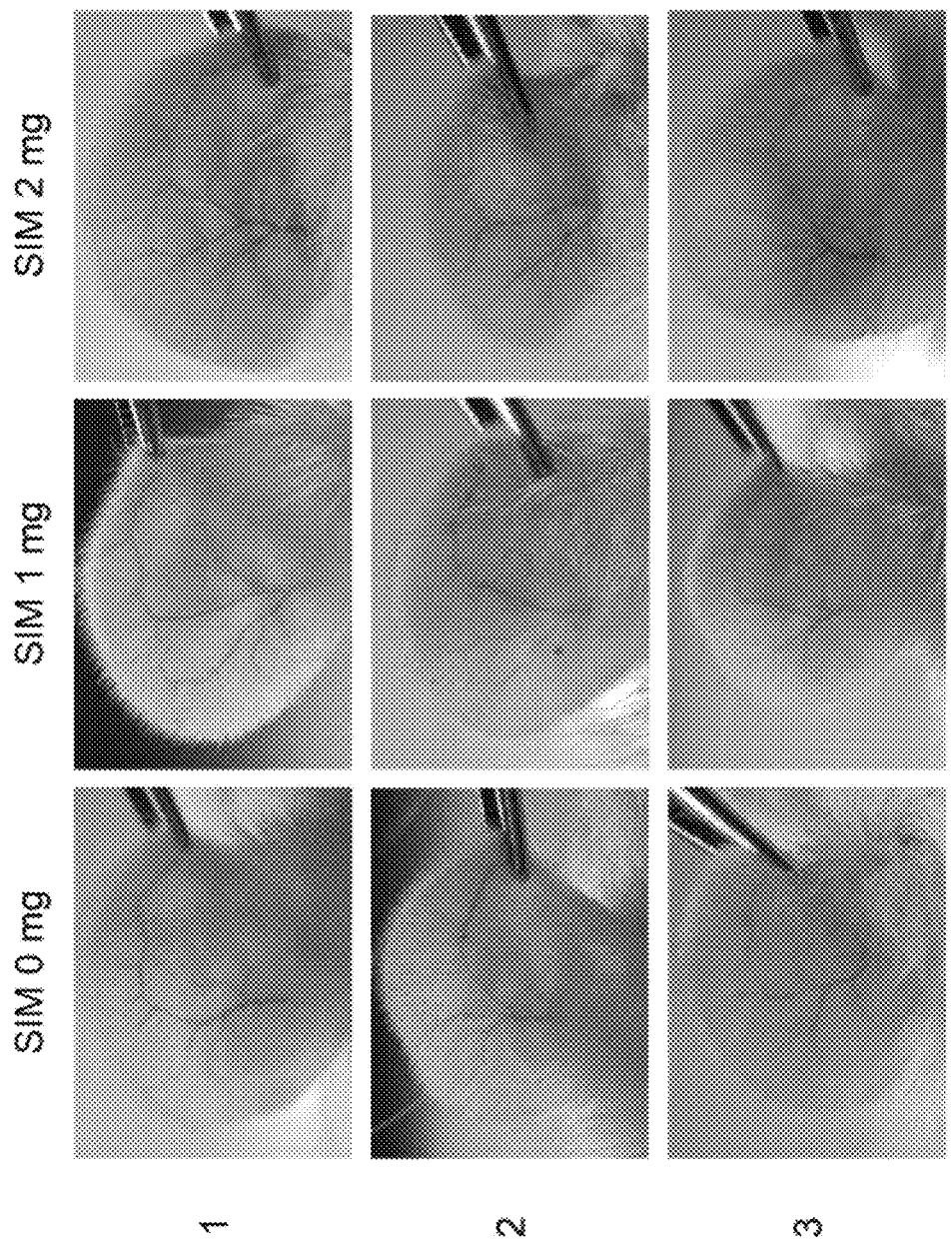
FIG. 4 shows that the local single intraosseous injection of a small dose of simvastatin improves microcirculation in type 1 diabetic rats.

Local Intraosseous Injection of Small Dose Simvastatin Promotes Systemic Angiogenesis In the STZ induced type 1 diabetic rat, we found that local single intraosseous injection of a small dose of simvastatin (1 mg or 2 mg) promotes angiogenesis, and the ear collateral circulation significantly increased 30 days later (see FIG. 4).

Figures 5A, 5B:
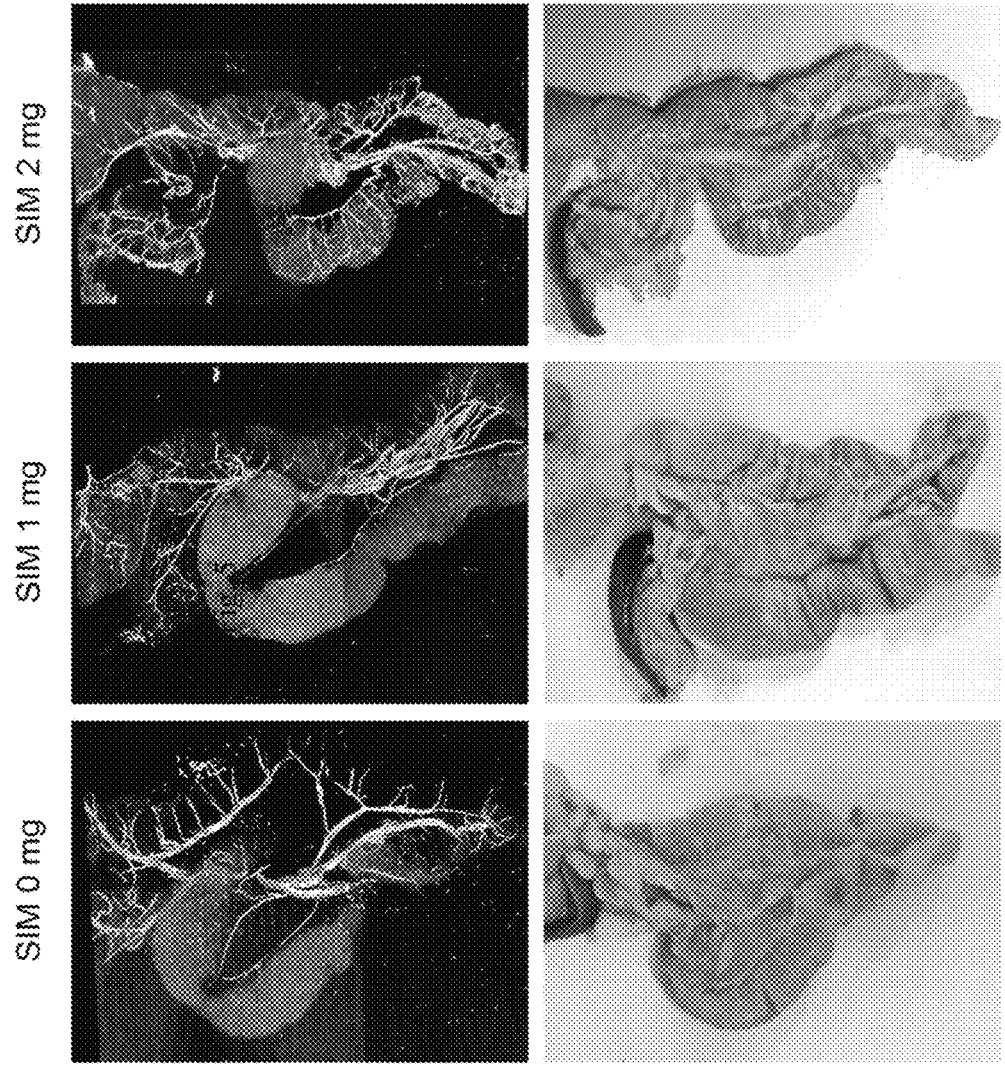
FIGS. 5A and 5B show that the local single intraosseous injection of a small dose of simvastatin improves angiogenesis around pancreas site in type 1 diabetic rats.

The rats were sacrificed before perfusion with MICROFIL®; and scanned using a micro-CT. The angiography results showed that the local pancreatic vessels were significantly increased in the group of intraosseous injection of simvastatin, and angiogenesis in the pancreas will protect islet cells (see FIG. 5).

Figure 6:
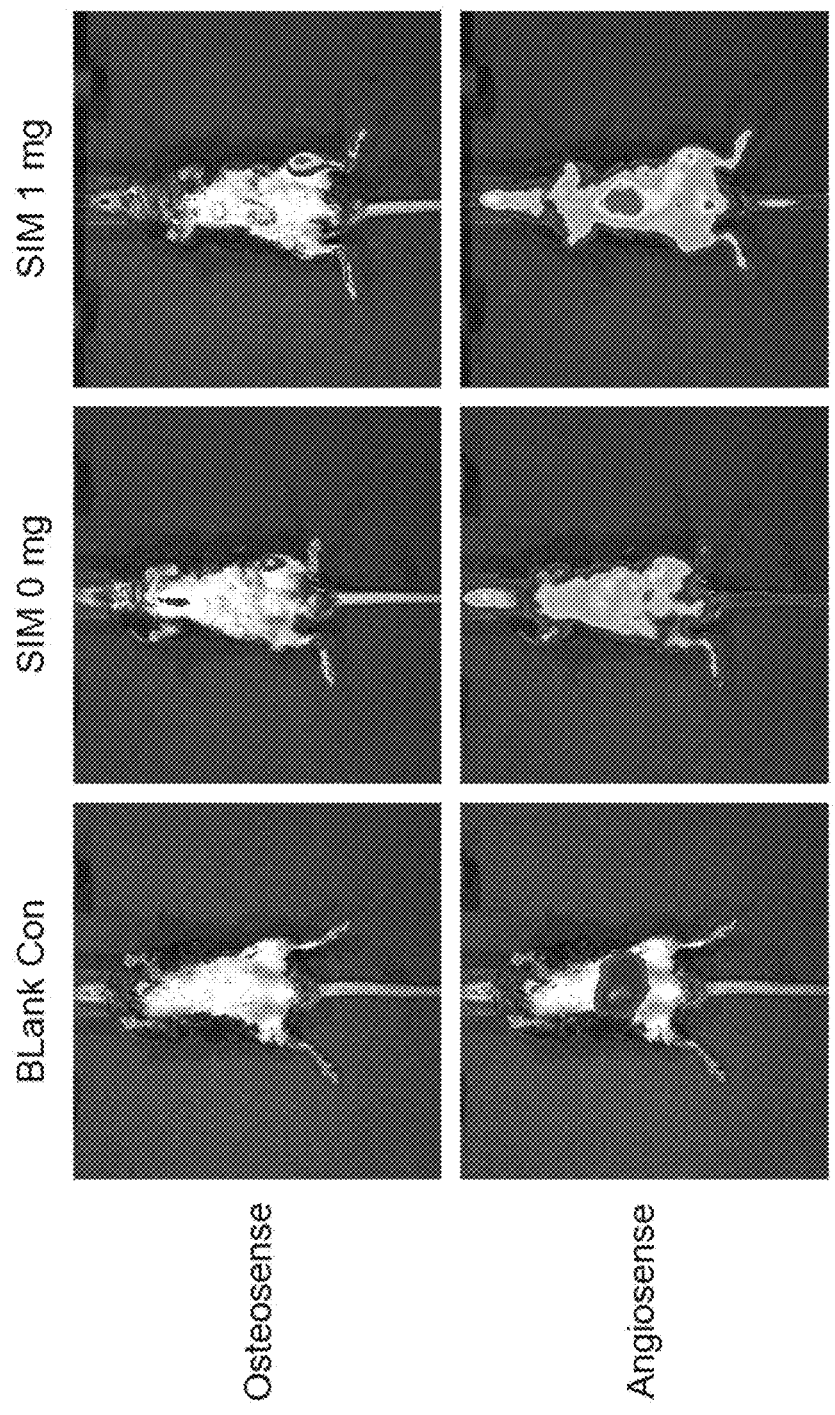
FIG. 6 shows that the local single intraosseous injection of a small dose of simvastatin improves systemic angiogenesis in type 1 diabetic rats.

C57 mice received local intraosseous injections of simvastatin 0 mg or 1 mg, four weeks after the tail vein injection of OSTEOSENSE® and ANGIOSENSE® fluorescent probes. The results showed that, 4 weeks after local intraosseous injection of simvastatin, the injection site was still active on bone formation, and the liver, spleen, kidney and pancreas were detected with strong vascular signals (see FIG. 6).

Example 4

Figures 1, 7:
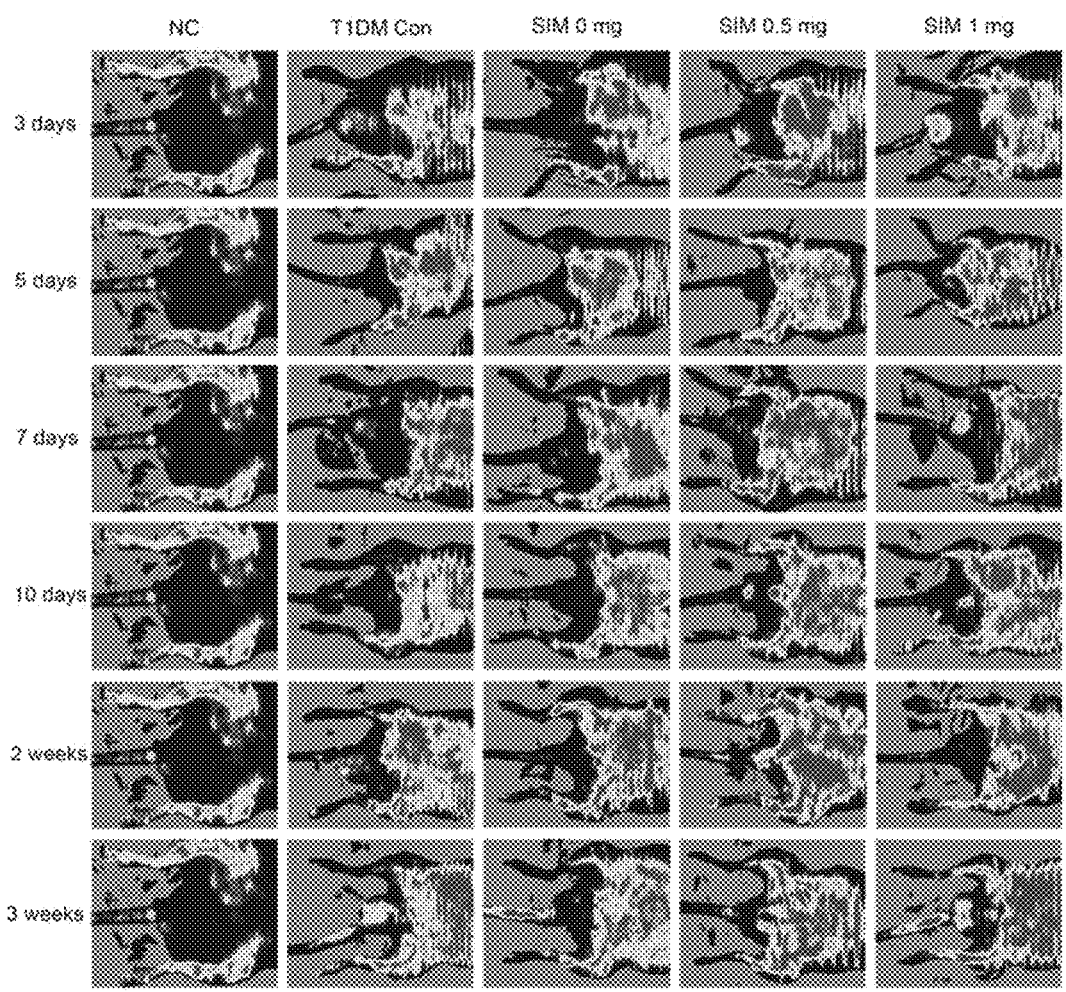
Figures 2, 7:
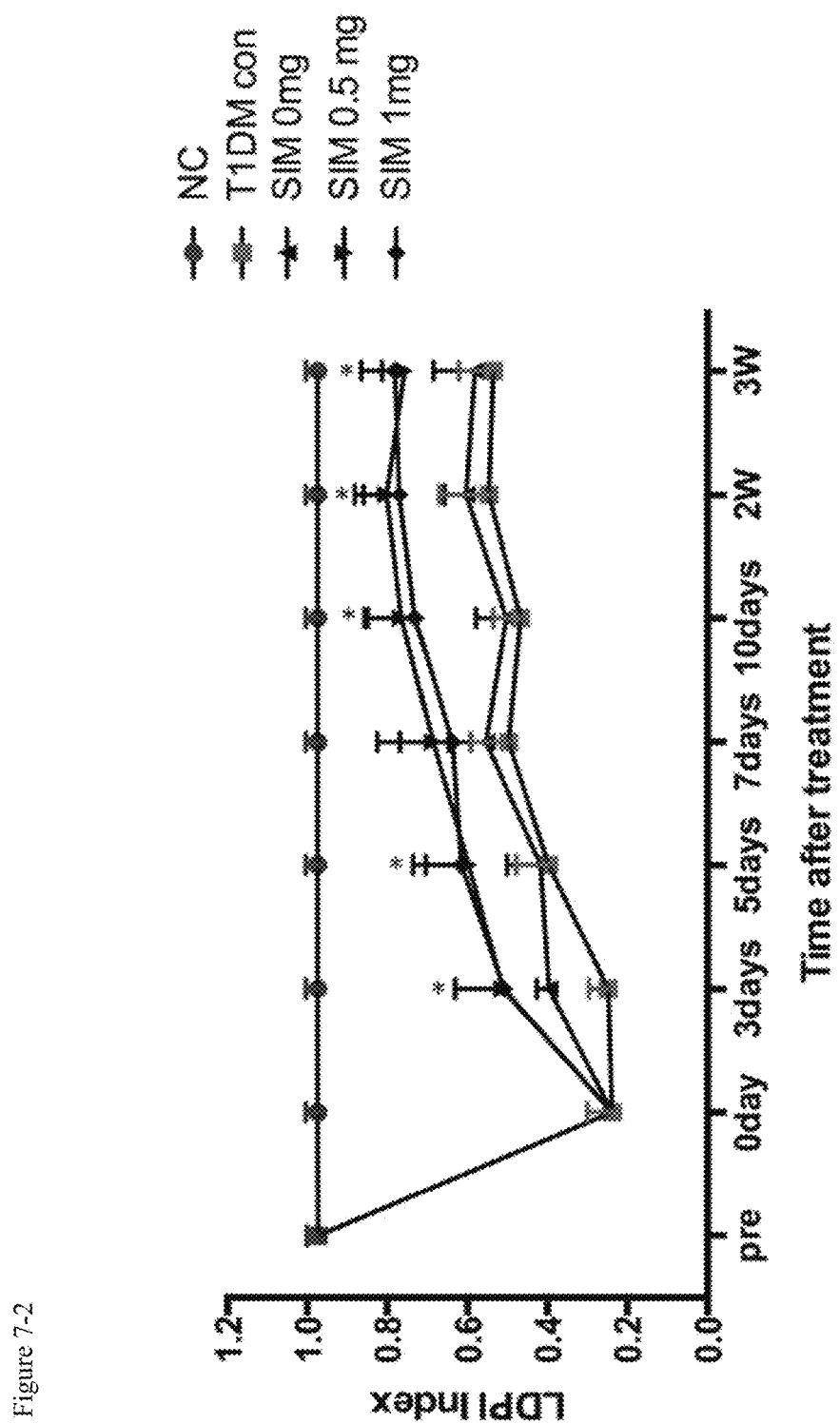

Local Intraosseous Injection of Small Dose Simvastatin Promotes Angiogenesis of the Contra-lateral Limb Ischemia of STZ Induced Type 1 Diabetic Rats In the STZ induced type 1 diabetic rats, the right side of the rat femoral artery was removed by 1.0 cm segment. The rat left tibia received a single local intraosseous injection of 0 mg, 0.5 mg, 1 mg of simvastatin respectively, and the ultrasonic Doppler blood flowmeter detected that local intraosseous injection of a small dose of simvastatin accelerates the recovery of blood flow speed ($P<0.01$); some blood recovery can be observed in 3 days (results see FIG. 7-1, 2).

Figure 2:
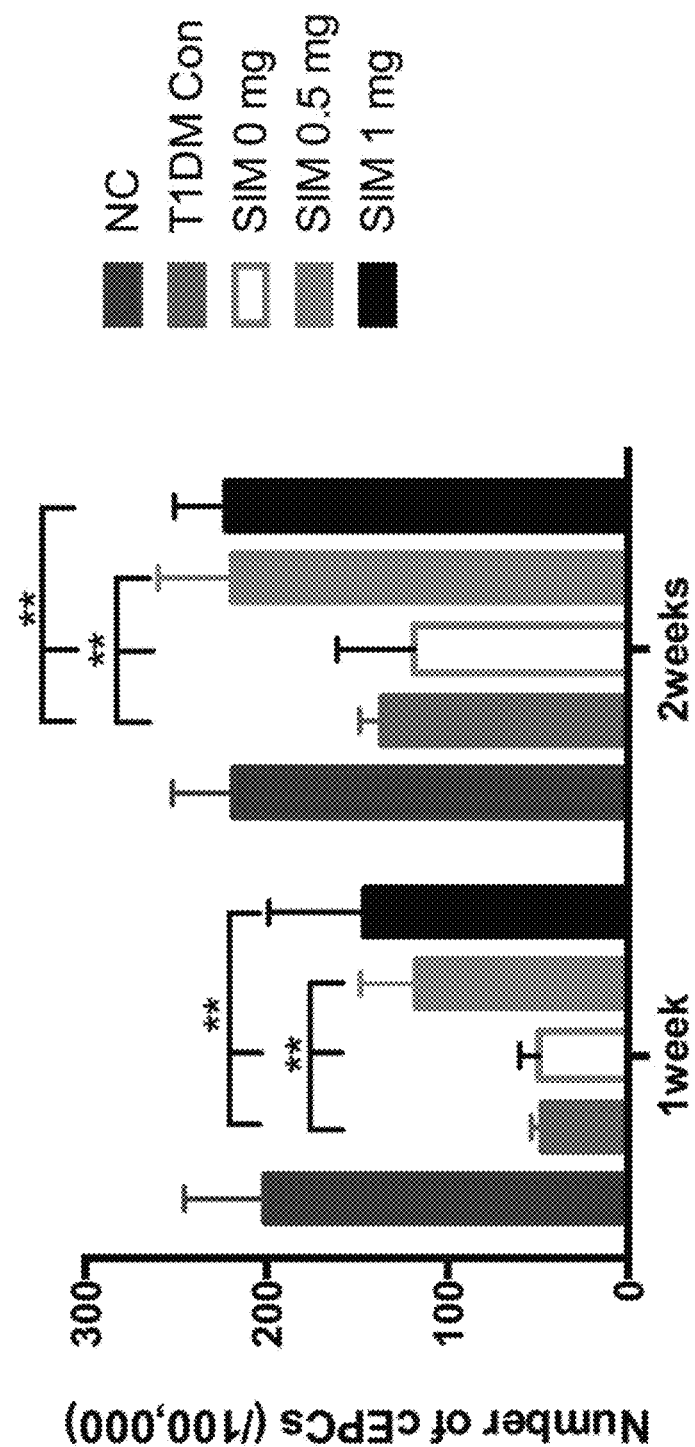
FIG. 2 shows that the local single intraosseous injection of a small dose of simvastatin promotes endogenous EPCs mobilization after hind limb ischemia in type 1 diabetic rats.
Figure 3:
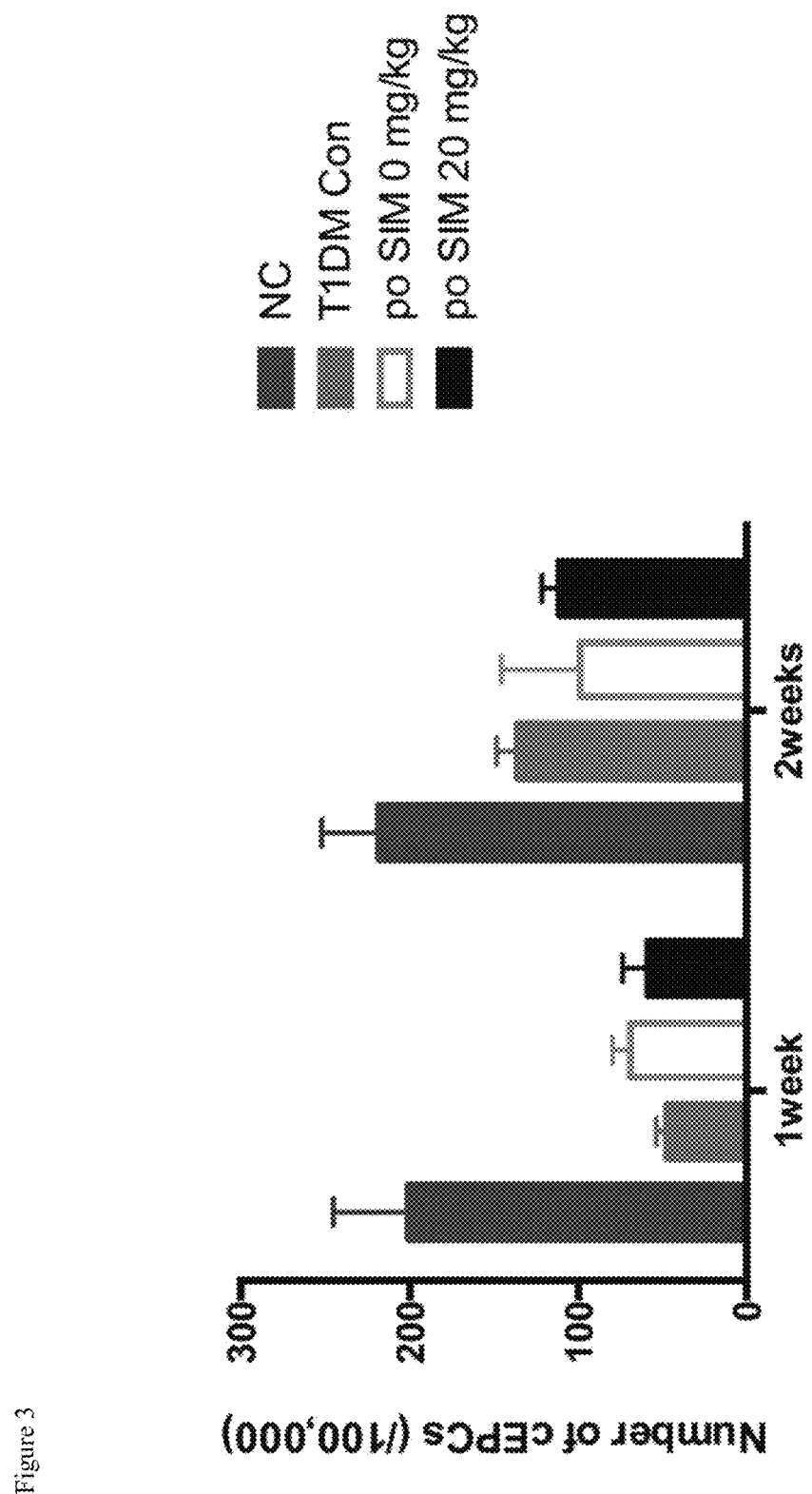
FIG. 3 shows the effect of oral administration of high dose of simvastatin on endogenous EPCs mobilization after hind limb ischemia in type 1 diabetic rats.
Figures 1, 8:
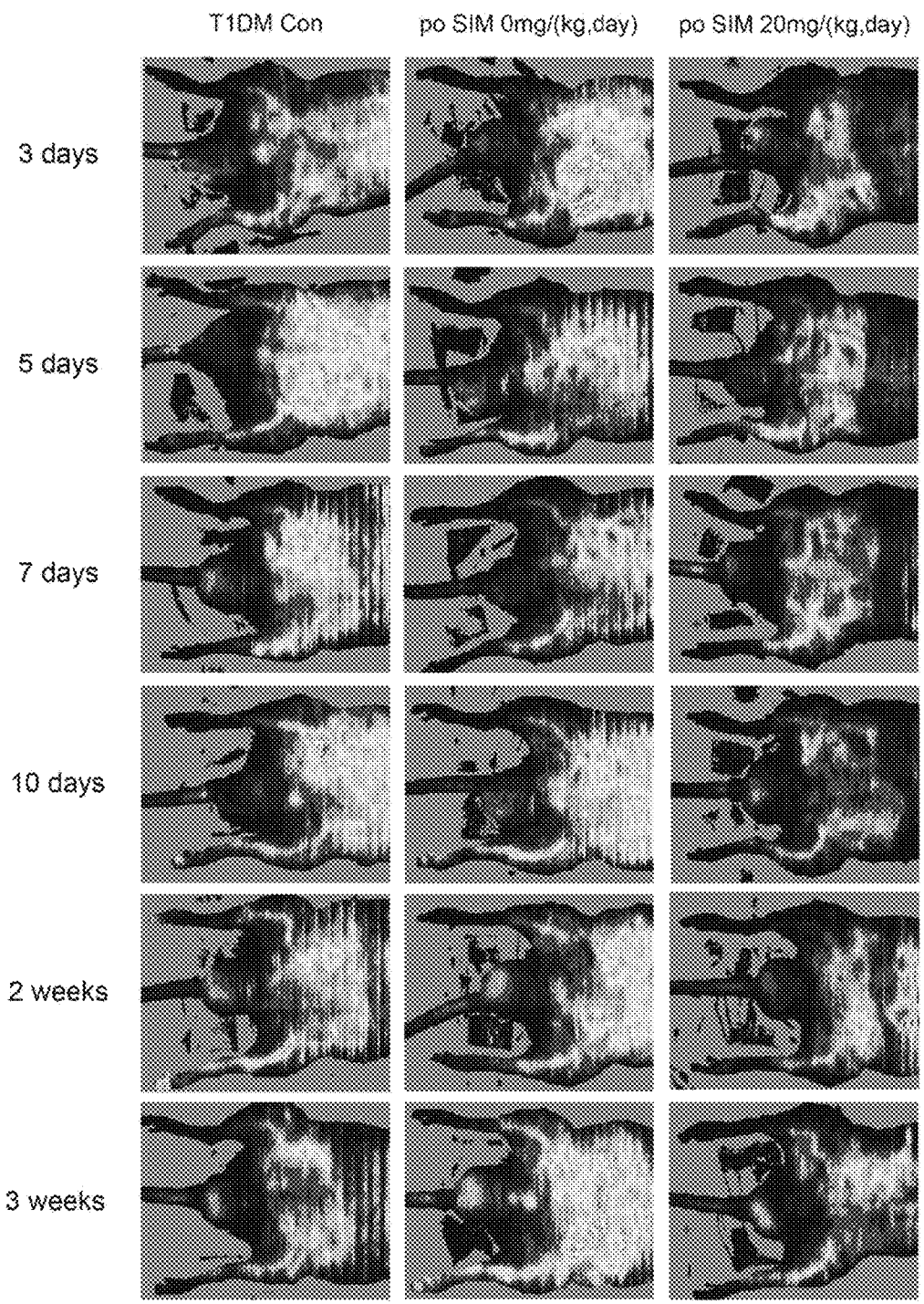
Figures 2, 8:
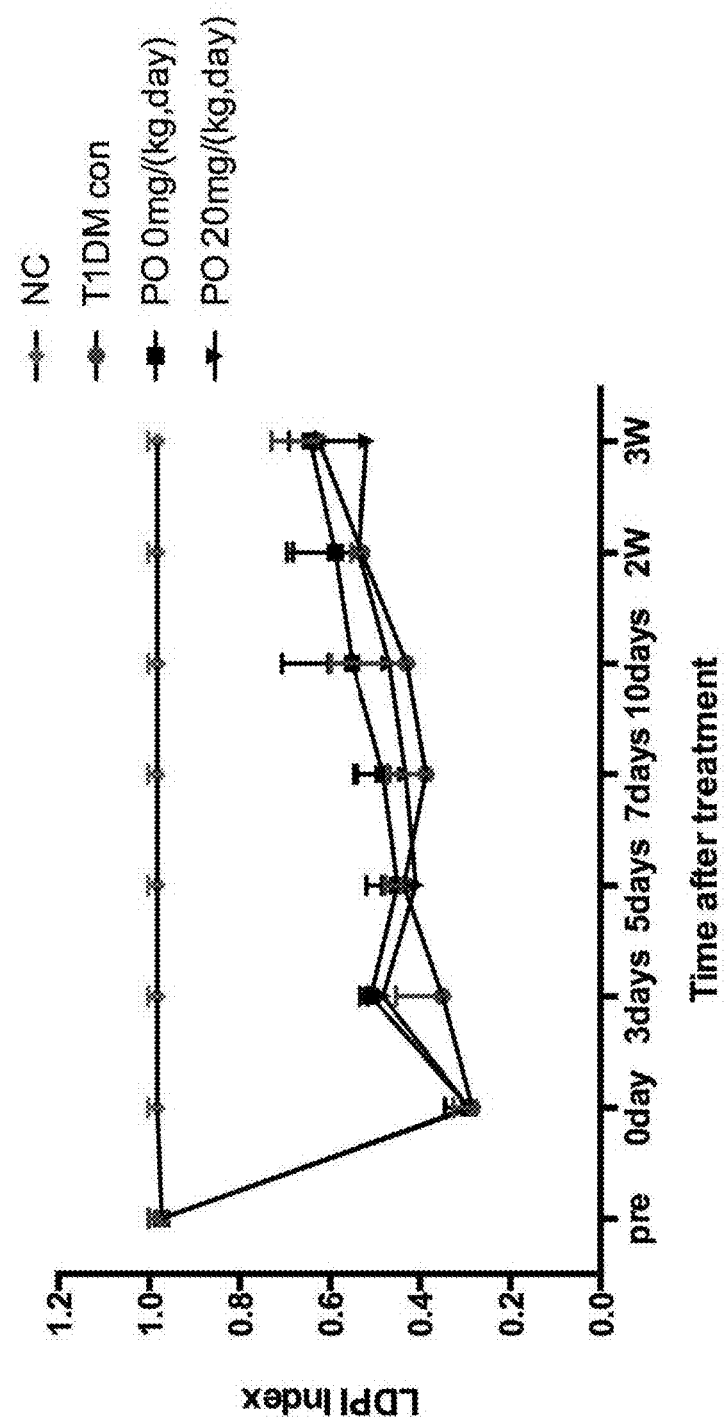

The STZ induced type 1 diabetic rat model of hind limb ischemia received daily gavage of 20 mg/kg/d simvastatin for 3 weeks, the results of the ultrasonic Doppler blood flowmeter showed that oral administration of simvastatin 20 mg/kg/d for 3 weeks did not significantly restore the blood flow velocity (see FIG. 8-1, 2).

Figures 9A, 9B:
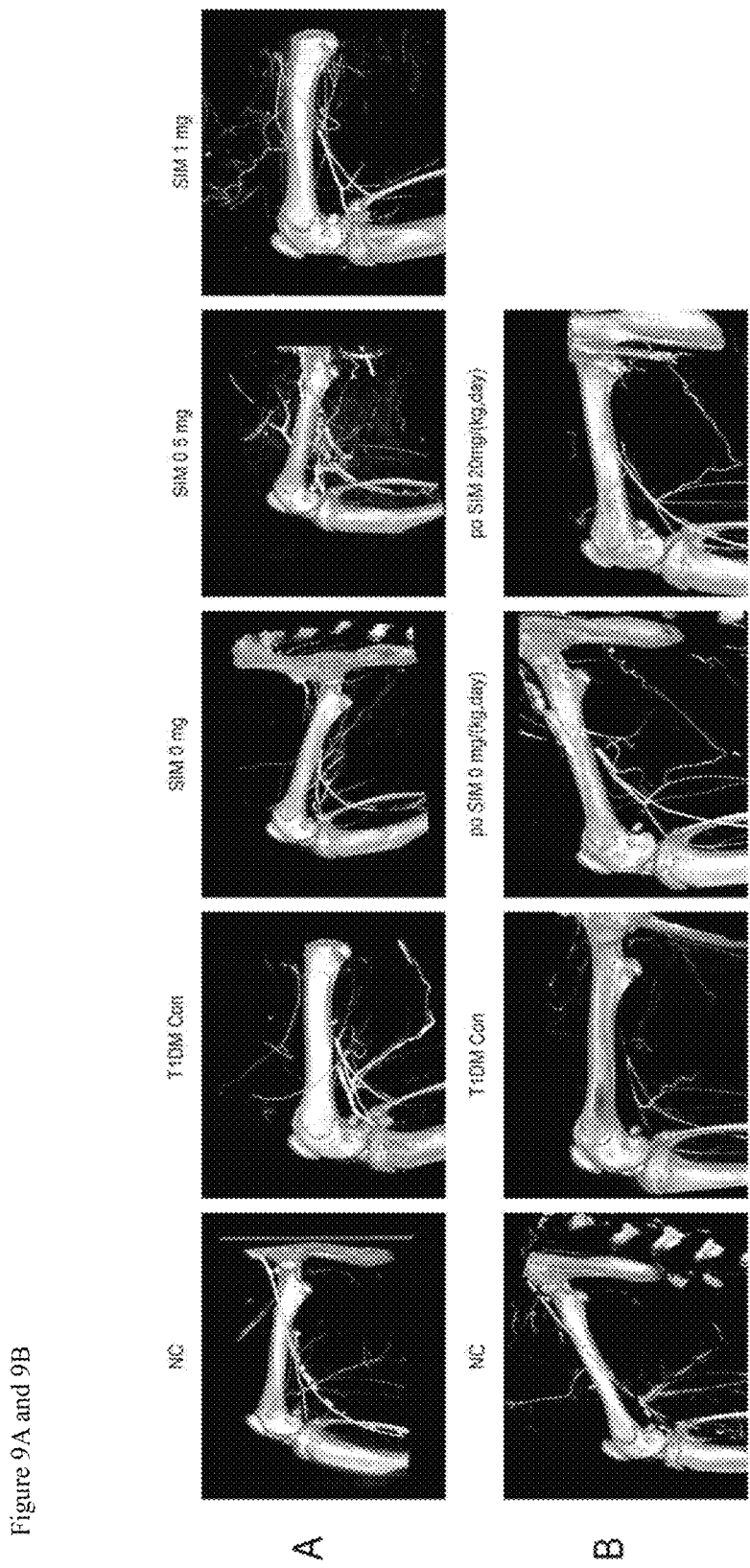
FIGS. 9A and 9B report the angiography results showing that the local intraosseous injection of a small dose of simvastatin significantly increased angiogenesis (FIG. 9A). In contrast, no angiogenesis was observed in the group of oral administration of high dose of simvastatin (FIG. 9B).

The rats were sacrificed before perfusion with MICROFIL®; and scanned using a micro-CT to observe the local pancreatic vessels. The angiography results showed that the local intraosseous injection of a small dose of simvastatin significantly increased angiogenesis, and there was more collateral circulation than the control group. There was no angiogenesis observed in the group of oral administration of high dose of simvastatin (see FIG. 9).

Example 5

Figure 10:
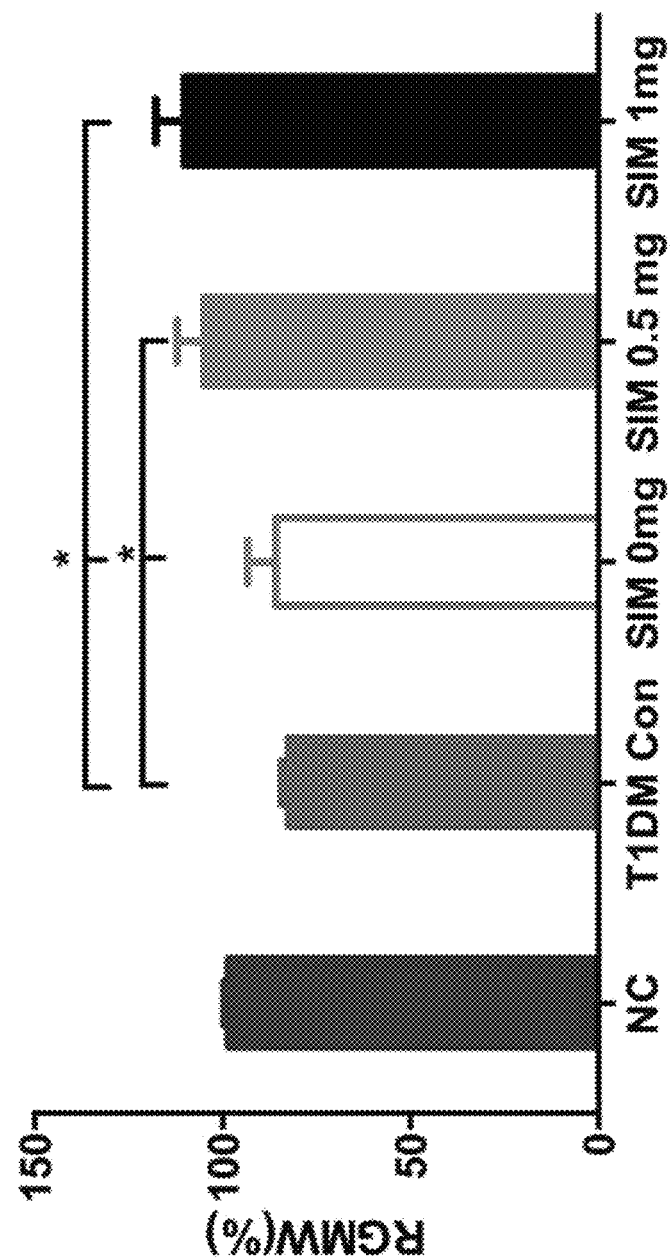
FIG. 10 shows that the local intraosseous injection of a small dose of simvastatin promotes the recovery of gastrocnemius atrophy induced by hind limb ischemia.

Local Intraosseous Injection of Small Dose Simvastatin Promotes Recovery of the Ratio of Wet Weight of Gastrocnemius In the STZ induced type 1 diabetic rats, the right side of the rat femoral artery was removed by 1.0 cm segment. The rat left tibia received a single local intraosseous injection of 0 mg, 0.5 mg, 1 mg of simvastatin respectively, and the gastrocnemius muscle was measured after 4 weeks. The results showed that the ischemic gastrocnemius wet weight significantly atrophied in the simvastatin 0 mg group ($P<0.05$), while there was no obvious atrophy in the group of local intraosseous injection of simvastatin 0.5 mg (see FIG. 10).

Example 6

Figures 11A, 11B, 11C, 11D:
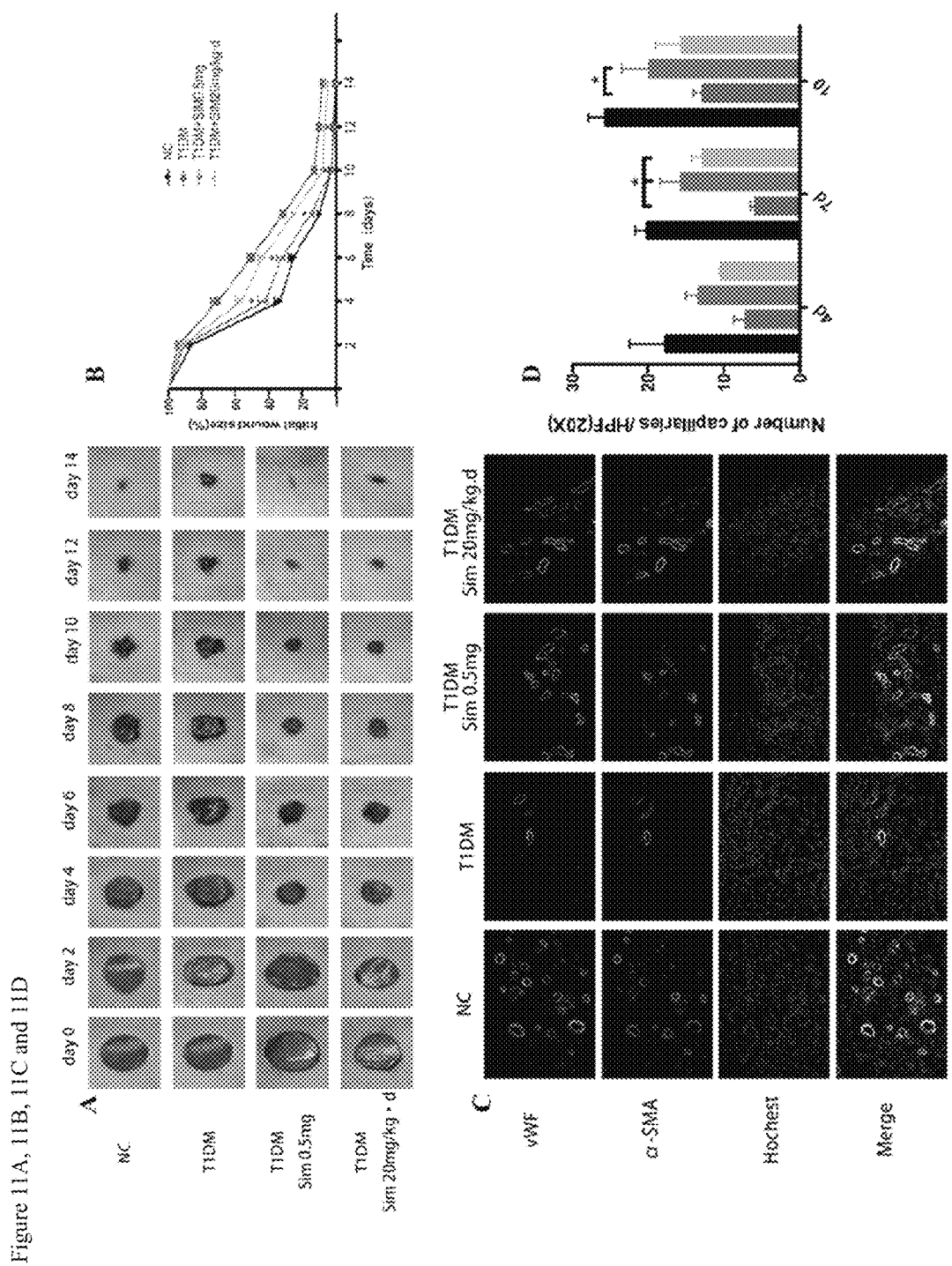
FIGS. 11A, 11B, 11C and 11D show that the local intraosseous injection of a small dose simvastatin promotes the skin wound healing in STZ induced type 1 diabetic rats.

Effect of Local Intraosseous Injection of Small Dose Simvastatin on Skin Wound Healing in STZ Induced Type 1 Diabetic Rats In the STZ induced Type 1 diabetic rats, a skin sampling device was used to cause a skin defect ($\varphi=12$ mm) on the back of the rats. The left tibia of rats received a local intraosseous injection of 0 mg, 0.5 mg simvastatin respectively. The results showed that the local intraosseous of simvastatin can significantly accelerate the skin defect recovery rate ($P<0.01$), and the effect is superior to that of oral high dose simvastatin (20 mg/kg/d). Immunofluorescence staining of new blood vessels also showed that simvastatin could significantly increase angiogenesis (see FIG. 11).

Example 7

Figures 12A, 12B, 12C:
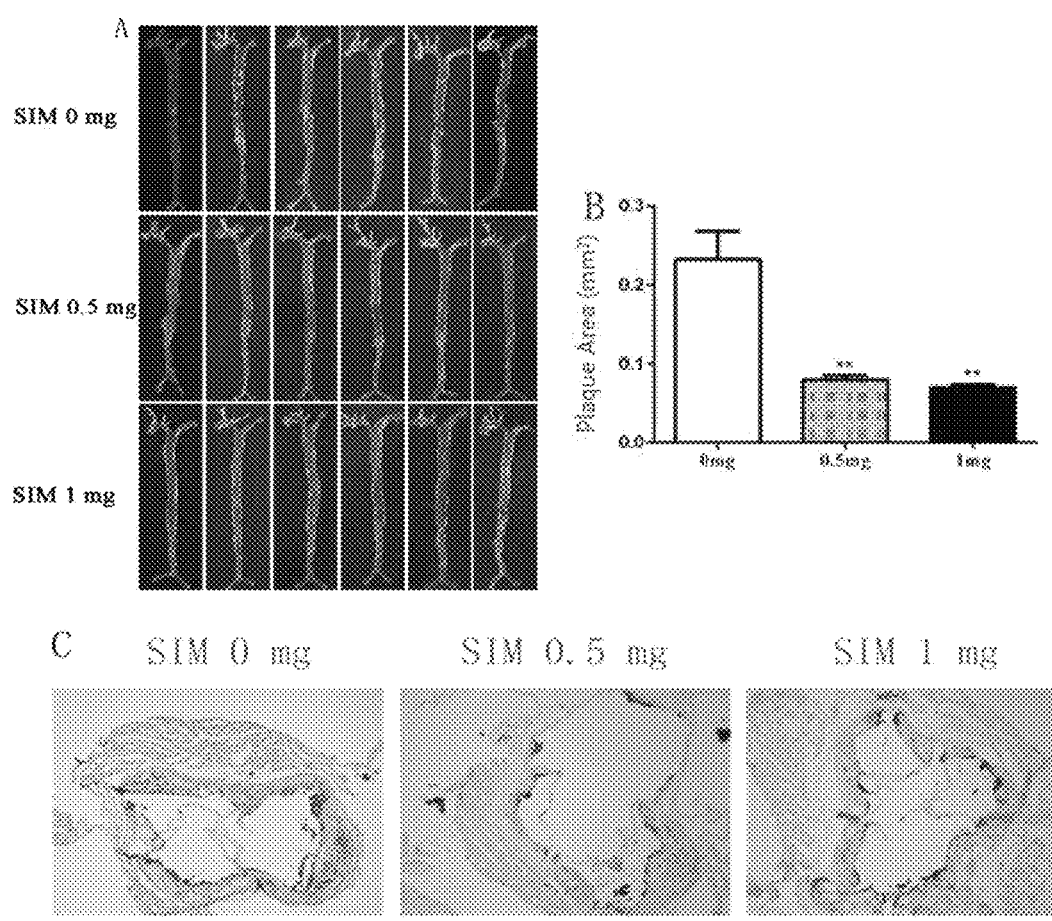
FIGS. 12A, 12B, 12C, 12D, 12E, 12F, 12G, 12H, 12I and 12J show the therapeutic effect of local single injection of a small dose of simvastatin on atherosclerosis in ApoE$^{-/-}$ mice.
Figures 12D, 12E, 12F, 12G, 12H, 12I:
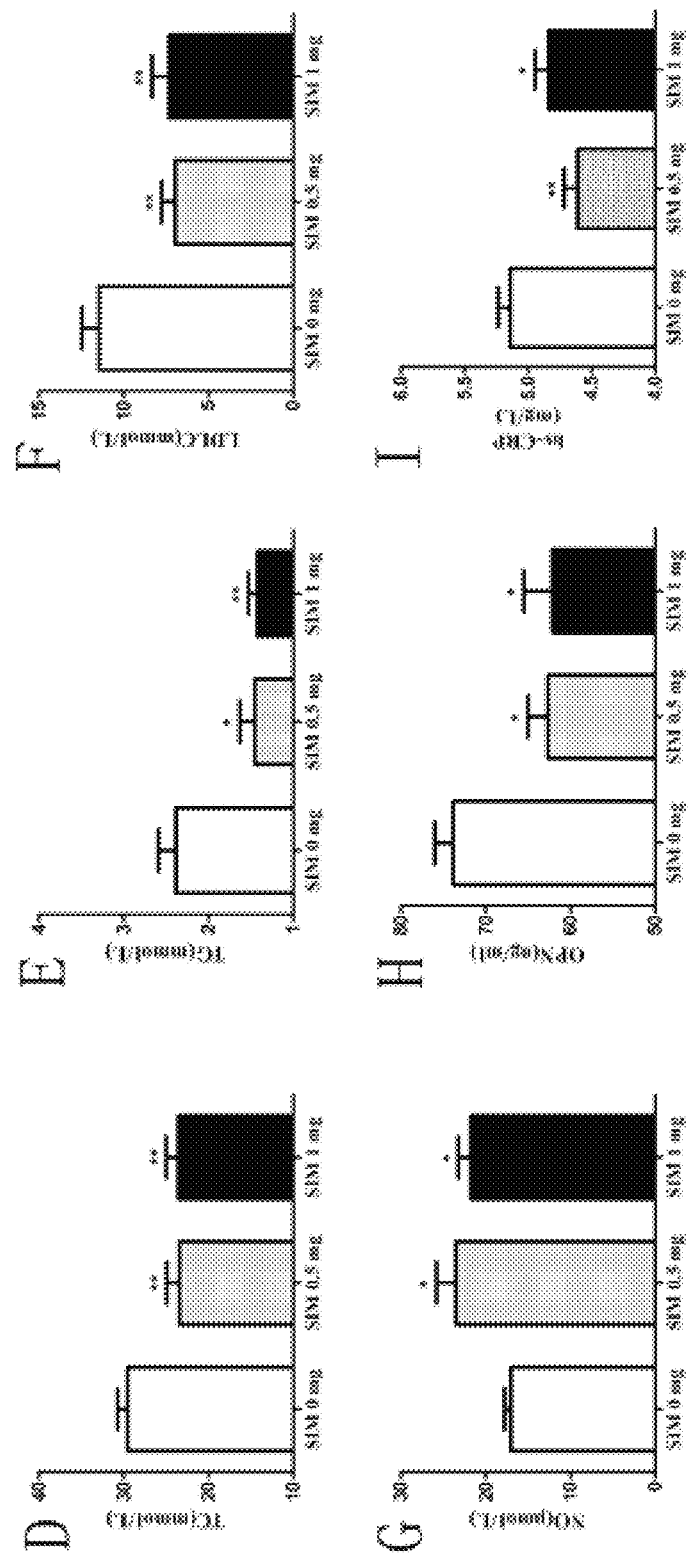
Figure 12J:
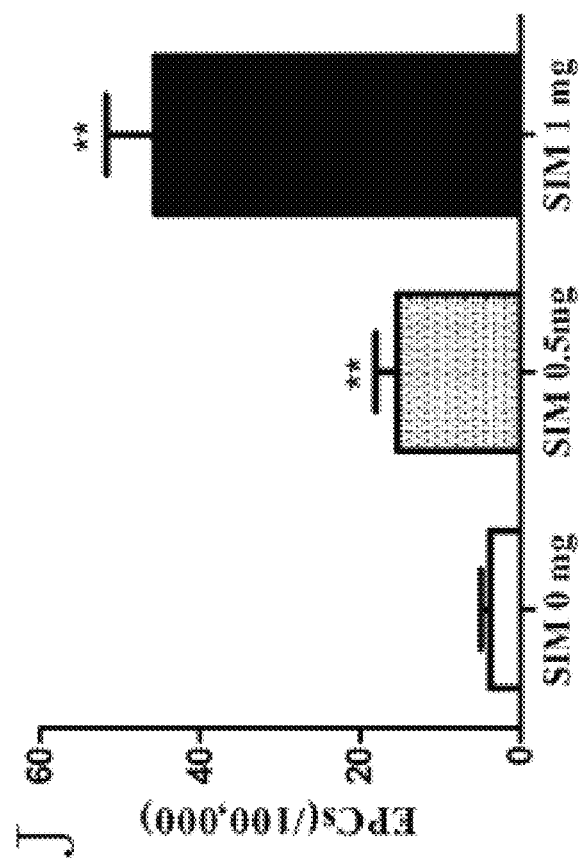

Therapeutic Effect of Local Single Intraosseous Injection of Small Dose Simvastatin on Atherosclerosis in ApoE−/− Mice The high fat diet induced atherosclerosis ApoE−/− mice received local single intraosseous injection of simvastatin (0 mg, 0.5 mg, 1 mg). The animals were euthanized 8 weeks later. The en face of aorta and aortic root continuous sections were stained by oil red O staining and image analysis software was used to compare the size of plaque, blood lipid concentrations were detected, the serum nitric oxide, osteopontin and hypersensitive C reaction protein was detected by ELISA, and the number of peripheral blood EPCs was detected by FACS. The results showed that in the local intraosseous injection of small dose simvastatin group, the plaque was significantly reduced, total cholesterol, triglyceride and low density lipoprotein cholesterol significantly decreased, osteopontin and high-sensitivity C-reactive protein concentration were significantly decreased; while the concentration of serum nitric oxide significantly increased. Most importantly, the number of EPCs in peripheral blood significantly increased (see FIG. 12).

Example 8

Figure 13:
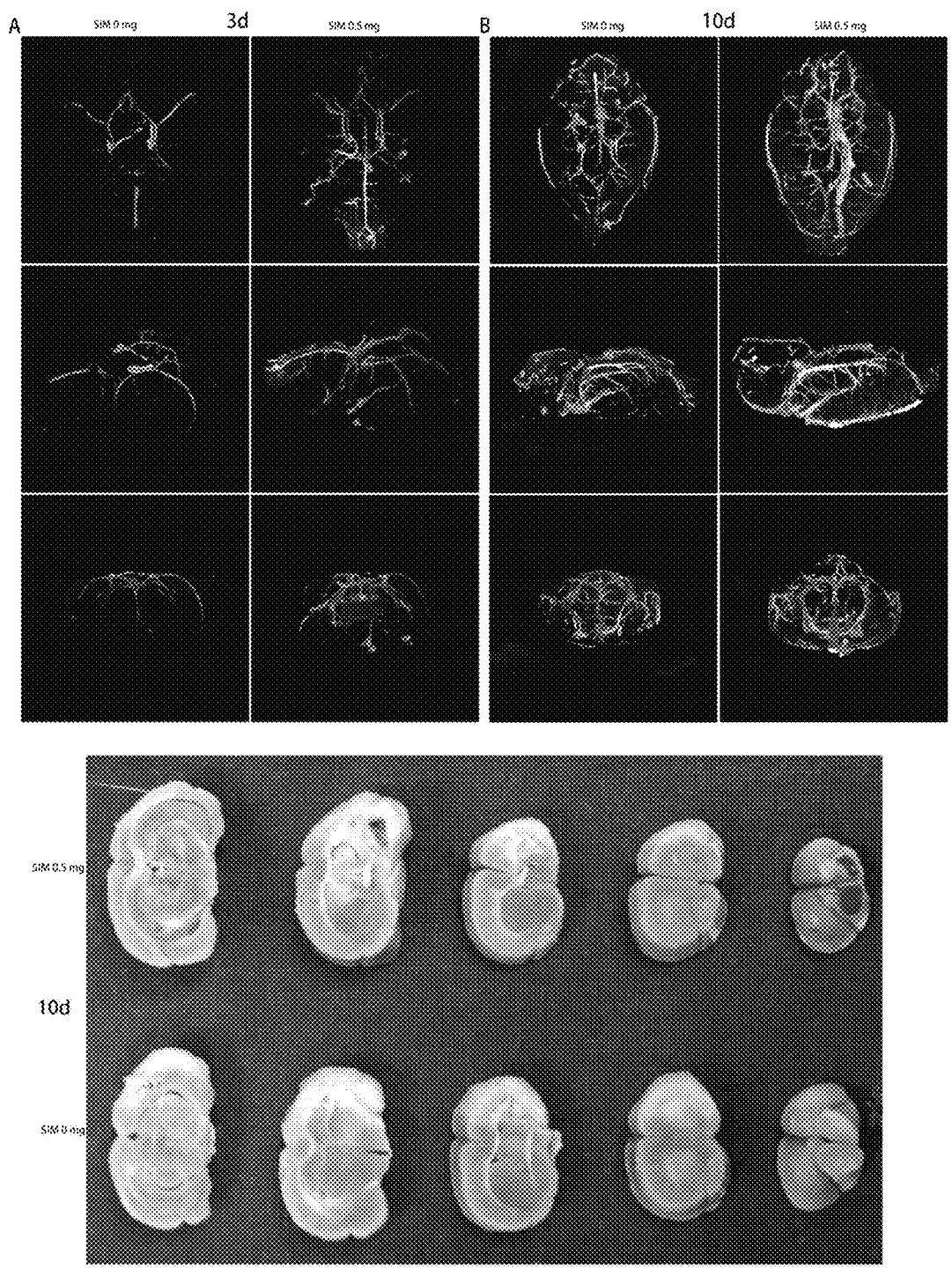
FIG. 13 shows that the local single intraosseous injection of a small dose of simvastatin promotes angiogenesis after middle cerebral artery occlusion in rats. Upper: angiograph of cerebral artery, lower: the TTC staining showing the ischemic area.

Local Single Intraosseous Injection of Small Dose of Simvastatin Promotes Angiogenesis after Middle Cerebral Artery Occlusion in Rats In rat middle cerebral artery occlusion (MCAo) induced cerebral ischemia animal models, the rats received a local single intraosseous injection of simvastatin 0.5 mg. Three days later, MICROFIL® perfusion and micro-CT scanning showed that in the experimental group, the collateral circulation reconstruction was significantly higher than that of the control group. TTC staining display infarct area was significantly lower than that in control group (see FIG. 13).

We claim:

1. A method of treating ischemic disease in a subject in need thereof comprising intraosseously administering to the subject in need thereof a composition comprising 0.1 mg to 50 mg of a statin or a pharmaceutically acceptable salt thereof, wherein said composition is administered by a single injection, and wherein the composition is administered once every 7 to 600 days.

2. The method of claim 1, wherein the statin is selected from the group consisting of simvastatin, atorvastatin, fluvastatin, lovastatin, pravastatin, rosuvastatin, pitavastatin, bervastatin, cerivastatin, crilvastatin, dalvastatin, mevasatin, tenivastatin and any combinations thereof.

3. The method of claim 1, wherein the statin is simvastatin.

4. The method of claim 1, wherein said composition further comprises a pharmaceutically acceptable carrier.

5. The method of claim 1, wherein said pharmaceutically acceptable salt of the statin is selected from the group consisting of hydrochloride, hydrobromide, hydriodate, sulfate, nitrate, phosphate, citrate, mesylate, trifluoroacetate, and acetate.

6. The method of claim 1, wherein the composition is administered once every 10 to 500 days.

7. The method of claim 1, wherein the composition is administered once every 30 to 300 days.

8. The method of claim 1, wherein the dose of the statin or pharmaceutically acceptable salt thereof ranges from 0.5 mg to 10 mg.

9. The method of claim 1, wherein said ischemic disease is peripheral ischemic disease.

10. The method of claim 1, wherein said ischemic disease is diabetic acromelic ischemic disease.

11. The method of claim 1, wherein the composition is administered once every 30 to 600 days.

12. The method of claim 1, wherein said ischemic disease is cardio-cerebrovascular ischemic disease.

\* \* \* \* \*